US006372216B1

(12) United States Patent
Piazza

(10) Patent No.: US 6,372,216 B1
(45) **Date of Patent: *Apr. 16, 2002**

(54) METHOD OF PRODUCING SPECIFIC IMMUNOGLOBIN TO BLOCK HCV INFECTION

(76) Inventor: Marcello Piazza, Via Mergellina n.35/d, I-80122 Naples (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,292
(22) PCT Filed: Feb. 24, 1997
(86) PCT No.: PCT/IT97/00037
§ 371 Date: Aug. 26, 1998
§ 102(e) Date: Aug. 26, 1998
(87) PCT Pub. No.: WO97/30729
PCT Pub. Date: Aug. 28, 1997

(30) Foreign Application Priority Data

Feb. 26, 1996 (IT) ...................................... 96-A/000013

(51) Int. Cl.[7] ......................... A61K 39/42; C07K 16/00

(52) U.S. Cl. ............................... 424/161.1; 424/130.1; 424/139.1; 424/159.1; 424/176.1; 530/387.1; 530/389.1; 530/389.4; 530/390.1

(58) Field of Search ........................... 424/130.1, 139.1, 424/159.1, 161.1, 176.1; 530/387.1, 389.1, 389.4, 390.1

(56) References Cited

U.S. PATENT DOCUMENTS 5,670,312 A * 9/1997 Santi ............................ 435/5
5,972,347 A * 10/1999 Eder et al. ............... 424/228.1

OTHER PUBLICATIONS

Farci et al. 1996 PNAS USA vol. 93 pp. 15394–15399 Dec. 1996.*
Farci et al.,"Hepatitis C virus: genetic heterogeneity and immunity", Trends in Experimental Clinical Medicine vol. 6 pp. 177–185 (1996).*
Bukh et al., "Genetic Hererogeneity of Hepatitis C Virus: Quasispecies and Genotypes", Seminars In Liver Disease vol. 15 No. 1 (1995) pp. 41–63.*
Piazza et al. Sexual Transmission of Hepatitis C Virus and Prevention with Intramuscular Immunoglobulin. 1998, AIDS Patient Care and STD's, vol. 12 No. 8 pp. 611–618.*
Who Technical Report Series, No. 840, pp. 34 to 99, "Requirements For The Collection, Processing And Quality Control Of Blood, Blood Components And Plasma Derivatives", 1994 (with remarks on the EPO International Preliminary Examination Report).

Krzysztof Krawczynski, et al., The Journal of Infectious Diseases, vol. 173, pp. 822 and 828, "Effect Of Immune Globulin On The Prevention Of Experimental Hepatitis C Virus Infection", 1996 (with AASLD Abstracts).
M. W. Yu, et al., International Meeting on Hepatitis C Virus and Related Viruses Molecular Virology and Pathogenesis, abs H13, p. 223, "Presence Of Protective Antibodies In An Experimental Intravenous Immune Globulin Prepared From Anti–HCV Positive Donor Units", Jun. 25—28, 1998.
K. Krawczynski, et al., Abstracts of 49th Annual Meeting AASLD, abs 398A and 944, "Early Termination Of HCV Infection By Passive Anti–HCV Transfer In Experimentally Infected Chimpanzees", Nov. 6 to 10, 1998.

Alfred M. Prince et al., "Sterilisation of Hepatitis and HTLV–III Viruses by Exposure to TRI(n–butyl)Phosphate and Sodium Cholate", *The Lancet*, Mar. 29, 1996, vol. 1, pp. 706–710.

Freja Ebeling, et al., "Tolerability and Kinetics to a Solvent–Detergent–Treated Intravenous Immunoglobulin Preparation in Hypogamma–Globulinaemia Patients," *Vox Sang*, 1995, vol. 69, pp. 91–94.

M.P.J. Piet et al., "The Use of Tri(n–butyl)phosphate Detergent Mixtures to Inactive Hepatitis Viruses and Human Immunodeficiency Virus in Plasma and Plasma's Subsequent Fractionation," *Transfusion*, vol. 30, No. 7, 1990, pp. 591–598.

Robert E. Louie et al, "Inactivation of Hepatitis C Virus in Low pH Intravenous Immunoglobulin," *Biologicals*, vol. 22, 13–19, 1994.

Richard I. Schiff, M.D., Ph.D., "Transmission of Viral Infections Through Intravenous Immune Globulin," *The New England Journal of Medicine*, vol. 331, No. 24, pp. 1649–1650, Dec. 15, 1994.

K. G. Reid, et al., "Potential Contribution of Mild Pepsin Treatment at pH4 to the Viral Safety of Human Immunoglobulin Products," *Vox Sang*, vol. 55, pp. 75–80, 1988.

Thomas Nowak, et al., "Virus Safety of Human Immunoglobulins: Efficient Inactivation of Hepatitis C and Other Human Pathogenic Viruses by the Manufacturing Procedure," *Journal of Medical Virology*, vol. 36, pp. 209–216, 1992.

J. L. Oncley, et al., "The Separation of the Antibodies, Isoagglutinins, Prothrombin, Plasminogen and $\beta_1$–Lipoprotein into Subfractions of Human Plasma," *J. Am. Chem. Soc.*, 1949, vol. 71, pp. 541–550.

(List continued on next page.)

*Primary Examiner*—Mary K. Zeman
(74) *Attorney, Agent, or Firm*—Oblon, Spivak, McClelland, Maier & Neustadt, P.C.

(57) ABSTRACT

A drug which protects individuals against hepatitis C virus (HCV) is made of HCV hyperimmune globulins, which guarantee a substantial hyperimmunity against HCV thanks to a substantial hyperconcentration of virus C neutralizing antibodies. This hyperconcentration is obtained from blood of a large number of anti-HCV positive blood donors. The material used for the preparation of the HCV hyperimmune globulins is made of up to 100% of anti-HCV positive blood units.

3 Claims, No Drawings

OTHER PUBLICATIONS

E. J. Cohn, et al., "Preparation and Properties of Serum and Plasma Proteins. IV. A System for the Separation into Fractions of the Protein and Lipoprotein Components of Biological Tissues and Fluids," *J. Am. Chem. Soc.*, vol. 68, 1946, pp. 459–475.

D. Y. Chien et al., "Persistence Of HCV Despite Antibodies To Both Putative Envelope Glycoproteins", *The Lancet*, Oct. 9, 1993, vol. 342, p. 933.

K. Krawczynski et al., "Studies On Protective Efficacy Of Hepatitis C Immunoglobulin (NGIO) In Experimental Hepatitis C Virus Infection", *Hepatology*, American Association for the Study of Liver Diseases Abstracts, Oct. 1994, No. 214, p. 110A.

Marcello Piazza et al., "Sexual Transmission Of The Hepatitis C Virus And Efficacy Of Prophylaxis With Intramuscular Immune Serum Globulin", *Archives of Internal Medicine*, Original Investigation, Jul. 28, 1997, vol. 157, No. 14. pp. 1537–1544.

Q.–L. Choo et al., "Vaccination Of Chimpanzees Against Infection By The Hepatitis C Virus", *Proc. Natl. Acad. Sci. USA*, Medical Sciences, Feb. 1994, vol. 91, pp. 1294–1298.

Domenico Rosa et al., "A Quantitative Test To Estimate Neutralizing Antibodies To The Hepatitis C Virus: Cytofluorimetric Assessment Of Envelope Glycoprotein 2 Binding To Target Cells", *Proc. Natl. Acad. Sci. USA*, Biochemistry, Mar. 1996, vol. 93, pp. 1759–1763.

Koji Ishi et al., "High Titers Of Antibodies Inhibiting The Binding Of Envelope To Human Cells Correlate With Natural Resolution Of Chronic Hepatitis C", *Hepatology*, American Association for the Study of Liver Diseases, Oct. 1998, pp. 117–1120.

Piero Pileri et al., "Binding Of Hepatitis C Virus To CD81", *Science*, Reports, Oct. 30, 1998, vol. 282, pp. 938–941.

Cees L. van der Poel et al., "Hepatitis C Virus Six Years On", *The Lancet*, Nov. 26, 1994, vol. 344, pp. 1475–1479.

Marcello Piazza, "Periodic Gammaglobulin To Prevent Hepatitis C In At–Risk Sexual Partners", *The Lancet*, Sep. 29, 1990, vol. 336, pp. 823–824.

P. Farci et al., "Immunity Elicited By Hepatitis C Virus", *Clinical and Experimental Rheumatology*, 1995, vol. 13 (Suppl. 13), pp. 9–12.

P. Farci et al., "Prevention Of Hepatitis C Virus Infection In Chimpanzees By Hyperimmune Serum Against The Hypervariable Region 1 Of The Envelope 2 Protein", *Proc. Natl. Acad. Sci. USA*, Medical Sciences, Dec. 1996, vol. 93, pp. 15394–15399.

\* cited by examiner

METHOD OF PRODUCING SPECIFIC IMMUNOGLOBIN TO BLOCK HCV INFECTION

The present invention relates to a drug adapted to protect individuals against the viral hepatitis infection.

It was only in the early 40's, in the U.S.A., that viruses (designated. "hepatitis A and hepatitis B viruses") capable of causing hepatitis were detected in samples of human blood. Individuals invariably recover from viral hepatitis A, whereas 5–10% of patients affected by viral hepatitis B do not recover, but go on to develop chronic hepatitis or become asymptomatic chronic carriers of the disease. The serum of patients who recover from viral hepatitis infection contains antibodies that neutralize the effect of the virus.

Consequently, in an attempt to protect individuals at-risk of contracting the infection, researchers began first to produce immune serum globulins and later vaccines.

When only hepatitis A and B viruses were known, all viral hepatitis infections not attributable to these viruses were called "nonA-nonB hepatitis". It is important to note that the hepatitis C virus (HCV) was discovered only about seven years ago and that it is the cause of the majority (80%) of parenterally transmitted nonA-nonB hepatitis cases.

Hepatitis C infection can be very severe because of its fatal sequelae, i.e., chronic hepatitis, liver cirrhosis and hepatocellular carcinoma. Only about 20–30% of infected individuals recover from the disease. Furthermore, infected subjects can transmit the infection to other individuals by means of their blood, the sexual route, etc.

It should be noted that most HCV-infected individuals are asymptomatic. Therefore, they are often unaware they have the infection and can transmit it to others.

While vaccines and specific immune preparations are used for the prevention of hepatitis A and B infection, there are at present no measures to protect all the many subjects exposed to the risk of acquiring HCV infection.

At present, HCV affects about 300 million people worldwide. Given the lack of effective protective measures, these infected individuals are a potential danger because they can spread this scourge through the world with devastating human, social and economic consequences.

The drug according to the present invention intends to make available to mankind a product that can effectively protect from HCV infection and is characterized by a substantial hyperimmunity against HCV, said hyperimmunity being due to a substantial hyperconcentration of virus C neutralizing antibodies.

Furthermore the drug according to the invention would be produced from blood units collected from HCV-infected individuals that contain a substantially high concentrations of HCV neutralizing antibodies. The final product would be safe because any HCV or any other possible infectious agents, that could be present in the blood units used for preparing the drug according to the invention, are inactivated by the Cohn method (alcohol fractionation) and/or by other possible virucidal treatments and/or additional methods capable of inactivating infectious agents.

At last, the use of the drug according to the invention is directed to substantially protect the individuals against HCV infection, such as, for example:

sexual partners of HCV-infected patients,
patients undergoing hemodialysis,
patients undergoing dental therapy or chiropodistry,
drug abusers,
patients affected by HCV-related fulminate hepatitis, liver cirrhosis or hepatocellular carcinoma undergoing liver transplantation,
etc, etc.

Additionally, the use of the drug according to the invention is also directed to substantially block HCV infection in all other possible conditions.

These and further features of the drug according to the invention will be apparent from the following description.

DESCRIPTION

The proposal of the drug according to the invention arose from an informed intuition later confirmed by experiments performed both in animals and in humans.

It is well known that blood is used also for the production of immune serum globulins (ISG or standard polyvalent ISG), that are present in plasma (the liquid part of blood) and are effective in preventing one or more infectious diseases. The starting material for the preparation of ISG is generally blood collected from at least 10,000 blood donors.

The mechanism of prevention obtained with ISG is the following: individuals affected by one or more infectious diseases (which can be clinically apparent or not) produce antibodies against those infectious agents and these antibodies are present in their blood. Some of these antibodies are defined "infection-related", because their presence is evidence of the infection, whereas other antibodies are defined "neutralizing", because they are able to destroy the agents that cause the infection.

For example, subjects infected by hepatitis A virus recover because they produce hepatitis A virus antibodies (i.e. hepatitis A virus neutralizing antibodies), that destroy the infectious agent. After recovery from the illness, the "memory" of this experience (infection) remains in the blood because hepatitis A virus neutralizing antibodies persist throughout the subject's life.

If the plasma of a subject who has recovered from hepatitis A infection (and which thus contains hepatitis virus A neutralizing antibodies) is administered to person who has never been exposed to hepatitis A virus and hence is susceptible to infection, the latter will be protected against this virus by virtue of these passively administered antibodies.

Because hepatitis A virus neutralizing antibodies, like most neutralizing antibodies against other infectious agents, are present only in a limited percentage of the population, the starting material for producing ISG, which is effective against several infectious agents, must be blood pooled from at least 10,000 blood donors. Protection from infection can also be obtained with "hyperimmune globulins" (i.e., specific immune globulins) that contain the same antibodies as ISG, except that the antibody against one particular infectious agent is present in high concentration (i.e., at least five-fold the concentration present in standard polyvalent ISG).

Hyperimmune globulin preparations are produced from the blood of donors specifically immunized with the relative vaccine or from blood donors who have recovered from the natural infection.

HCV infection is one of the most pressing health problems facing mankind today. About 300 million individuals worldwide are infected by this virus, many of whom die from liver cirrhosis or liver cancer. A fundamental problem in the fight against HCV infection is the existence of asymptomatic infected subjects, who are unaware they are affected and who are a potential source of infection for others.

Seven years ago Dr.M.Houghton and his research team (Chiron Corp., Emeryville, Calif., USA) identified the etiological agent of hepatitis C infection. This led to a breakthrough and for the first time a serological test became available that identified individuals infected by HCV. The diagnostic test is based on the detection of the antibodies induced by the virus (i.e., HCV antibodies). As mentioned above, these antibodies are infection-related antibodies and their presence in serum is merely a demonstration that the subject is HCV-infected.

Generally, the percentage of HCV-infected subjects varies from country to country and from continent to continent. In Italy the mean prevalence of HCV infection in the population is about 2%, it is lower in the USA and about 4.5% in Africa. It is important to emphasize that about 50% of the pooled blood samples used worldwide come from developing countries. Untill 1993 blood pooling centers did not discriminate HCV-infected blood donors from other donors. After 1993 most healthy authorities worldwide decreed that the anti-HCV positive blood units (i.e., blood containing infection-related antibodies) collected from HCV-infected donors should not to be used in pooled blood samples.

Thus, about 2% of blood units collected in Italy and 4.5% of blood units collected in Africa, etc., are discarded because they are anti-HCV positive. In Italy the law according to which all anti-HCV positive blood units are discarded came into effect in March 1993. After this date only anti-HCV negative blood units are used to prepare ISG.

On the intuition that ISG contain HCV neutralizing antibodies, before the tests to detect said HCV neutralizing antibodies were available, Piazza and co-workers, in a research that started in 1991 and ended in 1993, found that ISG produced from blood units, which were not screened for anti-HCV, protected the sexual partners of HCV-infected patients from the infection in a statistically significant fashion. Later in an experimental study on chimpanzees Houghton et al. showed that HCV induced the appearance of neutralizing antibodies, defined anti-gpE1/gpE2, that protected the chimpanzees from the infection. The neutralizing activity of these antibodies was confirmed by a reliable specific test (neutralization of binding assay).

The unscreened ISG used by Piazza in his clinical study and some lots of screened ISG produced after 1993 were tested to verify if they contained the anti-gpE1/gpE2 neutralizing antibodies.

The results of this study were striking:
a) all the lots of ISG produced from blood units pooled from donors unscreened for anti-HCV contained high titers of HCV neutralizing antibodies;
b) no HCV neutralizing antibodies were detected in any of the lots of screened ISG currently on the market, which are produced exclusively from anti-HCV negative blood units.

Piazza then asked to himself which was the difference between the unscreened ISG preparations which contain HCV neutralizing antibodies and the screened ISG preparations which do not contain said HCV neutralizing antibodies.

Piazza intuited that the difference consists only in the fact that the unscreened ISG contain a small (about 2%) percentage of anti-HCV positive blood units, whereas the screened ones do not contain said anti-HCV positive blood percentage. Thus it is logical, as Piazza intuited, that the HCV neutralizing antibodies are contained only in that small aliquot of anti-HCV positive blood units (2%) which are now, by law, discarded.

Piazza then asked to himself. "If said anti-HCV positive blood units, which are now discarded, were utilized for the preparation of immune globulins, would the HCV neutralizing antibodies (anti-gpE1/gpE2 and/or other type of HCV neutralizing antibodies) contained in said immune globulins be substantially hyperconcentrated?"

The hypothesis and the intuition prompted the idea of producing hyperimmune globulins against the hepatitis C virus using as source material only the anti-HCV-positive blood units, which at present are discarded. HCV hyperimmune globulins that are produced from up to 100% of anti-HCV-positive blood units will contain an even higher titer of HCV neutralizing antibodies than the pre-1993 immune serum globulins, which were produced from blood units containing only 2% of anti-HCV positive blood units.

HCV hyperimmune globulins so produced would contain a mean HCV neutralizing antibody titer about fifty-fold higher than that present in the pre-1993 immune serum globulins that were effective in preventing HCV infection in sexual partners of HCV-infected patients. In order to obtain HCV hyperimmune globulins with even higher HCV neutralizing antibody titers, only those anti-HCV positive blood units containing very high titers of HCV neutralizing antibodies should be utilized as starting material.

Obviously hyperimmune globulins against HCV should be prepared from blood of a very large number of anti-HCV positive blood donors in order to obtain a wide range of heterogeneous neutralizing antibodies to the different strains of HCV.

Besides protecting from infection sexual partners of HCV-infected patients, these HCV hyperimmune globulins could be used in many other situations in which individuals are exposed to the risk of acquiring HCV infection, e.g. patients undergoing hemodialysis, patients undergoing dental therapy or chiropodistry, drug abusers, etc.

Finally, HCV hyperimmune globulins would be of great benefit in preventing HCV reinfection after liver transplantation in patients affected by HCV-related fulminant hepatitis, liver cirrhosis or hepatocellular carcinoma. In fact, a major complication in these patients is given by the reinfection of the transplanted liver by HCV.

Additionally, HCV hyperimmune globulins could also be used to substantially block HCV infection in all other possible conditions.

Other important advantages, which should be taken into account, are that anti-HCV positive blood donors, who are now excluded from donating their blood, will feel in the future socially useful. In addition, the HCV-infected patients themselves will be able to enjoy a social life unconditioned by the thought they may affect their partners. The drug according to the invention, herein referred to as HCV hyperimmune globulins, will cost much less to produce than other hyperimmune globulins currently used for other infectious agents. Moreover, the costs of disposing of anti-HCV positive blood units represent a further saving.

At last, the drug according to the invention is safe. In fact, immune serum globulins prepared for intramuscular use by Cohn method (alcohol fractionation, which inactivates both HCV and other infectious agents) have been safely used throughout the world for over 50 years. Virucidal treatments and/or additional methods capable of inactivating infectious agents can also be added to production process, in order to assure further the safety of the final product. HCV hyperimmune globulin preparations are intended not only for intramuscular use but also for intravenous use.

What is claimed is:
1. A method of producing an antibody composition, wherein said antibody composition (1) contains a substantial hyperconcentration of a multiplicity of hepatitis C virus neutralizing antibodies effective to neutralize different strains of hepatitis C virus and (2) blocks hepatitis C virus infection in subjects infected with hepatitis C virus, comprising:

(a) obtaining anti-hepatitis C virus-positive blood units which contain high titers of hepatitis C virus neutralizing antibodies from a multiplicity of anti-hepatitis C virus-positive blood donors;

(b) pooling the blood units which contain high titers of hepatitis C virus neutralizing antibodies to form a pooled plasma which contains a high titer of hepatitis C virus neutralizing antibodies; and (c) fractioning the pooled plasma to produce the antibody composition wherein infectious agents in the composition have been inactivated.

2. The method of claim 1, wherein thousands of anti-hepatitis C virus positive blood units which contain high titers of hepatitis C virus neutralizing antibodies are pooled to produce said pooled plasma.

3. The method of claim 1, wherein said fractioning is accomplished by alcohol fractionation.

* * * * *

UNITED STATES PATENT AND TRADEMARK OFFICE
CERTIFICATE OF CORRECTION

PATENT NO.    : 6,372,216 B1
DATED         : April 16, 2002
INVENTOR(S)   : Piazza It is certified that error appears in the above-identified patent and that said Letters Patent is hereby corrected as shown below:

<u>Title page, Item [54] and Column 1,</u>
The Title should read:
-- [54] METHOD OF PRODUCING SPECIFIC IMMUNOGLOBULIN TO BLOCK HCV INFECTION --

Signed and Sealed this

Second Day of July, 2002

*Attest:*

*Attesting Officer*

JAMES E. ROGAN
*Director of the United States Patent and Trademark Office*